United States Patent
Chomas

(10) Patent No.: US 8,043,219 B2
(45) Date of Patent: Oct. 25, 2011

(54) AUTOMATED POWER LEVEL FOR CONTRAST AGENT IMAGING

(75) Inventor: James E. Chomas, San Francisco, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 2013 days.

(21) Appl. No.: 10/944,072

(22) Filed: Sep. 17, 2004

(65) Prior Publication Data
US 2006/0064018 A1  Mar. 23, 2006

(51) Int. Cl.
*A61B 8/14* (2006.01)

(52) U.S. Cl. ............... 600/458; 600/437; 600/454

(58) Field of Classification Search .......... 600/458, 600/437, 454
See application file for complete search history.

(56) References Cited

U.S. PATENT DOCUMENTS

| | | | |
|---|---|---|---|
| 5,410,516 A | 4/1995 | Uhlendorf et al. | |
| 5,456,257 A * | 10/1995 | Johnson et al. | 600/458 |
| 5,469,849 A * | 11/1995 | Sasaki et al. | 600/443 |
| 5,482,046 A * | 1/1996 | Deitrich | 600/458 |
| 5,577,505 A * | 11/1996 | Brock-Fisher et al. | 600/458 |
| 5,675,554 A | 10/1997 | Cole et al. | |
| 5,944,666 A * | 8/1999 | Hossack et al. | 600/458 |
| 6,045,506 A * | 4/2000 | Hossack | 600/443 |
| 6,080,107 A * | 6/2000 | Poland | 600/458 |
| 6,113,544 A * | 9/2000 | Mo | 600/447 |
| 6,224,554 B1 | 5/2001 | Tickner et al. | |
| 6,340,348 B1 * | 1/2002 | Krishnan et al. | 600/447 |
| 6,368,279 B1 | 4/2002 | Liu | |
| 6,398,732 B1 * | 6/2002 | Brock-Fisher et al. | 600/443 |
| 6,398,733 B1 | 6/2002 | Simopoulos et al. | |
| 6,398,735 B1 | 6/2002 | Clark | |
| 6,413,218 B1 * | 7/2002 | Allison et al. | 600/443 |
| 6,491,633 B1 * | 12/2002 | Krishnan et al. | 600/447 |
| 6,497,665 B1 * | 12/2002 | Hunt et al. | 600/458 |
| 6,497,666 B1 * | 12/2002 | Phillips et al. | 600/458 |
| 6,503,203 B1 * | 1/2003 | Rafter et al. | 600/458 |
| 6,512,854 B1 * | 1/2003 | Mucci et al. | 382/275 |
| 6,527,718 B1 * | 3/2003 | Connor et al. | 600/439 |
| 6,533,728 B1 | 3/2003 | Belohlavek et al. | |
| 6,537,218 B1 * | 3/2003 | Simopoulos et al. | 600/447 |
| 6,544,184 B1 * | 4/2003 | Guracar | 600/458 |
| 6,547,738 B2 | 4/2003 | Lysyansky | |
| 6,561,982 B2 * | 5/2003 | Greppi et al. | 600/458 |
| 6,641,538 B2 | 11/2003 | Nakaya | |
| 6,680,107 B2 | 1/2004 | Yagihashi et al. | |
| 6,740,039 B1 * | 5/2004 | Rafter et al. | 600/439 |
| 6,899,681 B1 * | 5/2005 | Phillips et al. | 600/458 |
| 2003/0028098 A1 * | 2/2003 | Brock-Fisher | 600/431 |
| 2003/0158479 A1 * | 8/2003 | Li et al. | 600/437 |
| 2004/0087858 A1 * | 5/2004 | Hao et al. | 600/458 |
| 2005/0038340 A1 * | 2/2005 | Vaezy et al. | 600/439 |

* cited by examiner

*Primary Examiner* — Brian Casler
*Assistant Examiner* — Joseph M Santos

(57) ABSTRACT

Automated determination and setting of an ultrasound system transmit power level is provided for contrast agent imaging. Low mechanical index imaging of contrast agents allows substantially continuous imaging of contrast agents without destruction. By comparing data associated with different transmit power levels and spatial locations, different delays between acquisition or different acquisition sequences, a contrast agent imaging transmit power generally minimizing destruction of contrast agents and maximizing signal-to-noise ratio is automatically determined. By using contrast agent specificity for setting the transmit power in addition or alternative to destruction of contrast agents, harmonic imaging may be improved.

4 Claims, 7 Drawing Sheets

AUTOMATED POWER LEVEL FOR CONTRAST AGENT IMAGING

BACKGROUND

The present invention relates to contrast agent imaging. In particular, a transmit power level is provided for contrast agent ultrasound imaging.

Contrast agents are typically gas or fluid filled microspheres which resonate at ultrasound frequencies. The contrast agents are injected into the blood stream and carried to various locations in the body. When insonified, echo signals are generated due to resonance of the contrast agents. The echo signals provide good contrast to signals from the surrounding tissue or fluid.

Destruction of contrast agents prevents repetitive scanning or real-time imaging. At higher powers, pressures, or mechanical indices (MI), the micro-spheres can burst and be eliminated from a scanning plane. Since contrast agents can move slowly through the body's vasculature, the micro-spheres do not quickly enter the imaged tissue. With high MI imaging, slower scanning rates are required to allow fresh agent to replenish the scanning plane.

Contrast agents are imaged with low MI or low transmitted power levels to avoid destruction. High frame rates for imaging can be maintained. For low MI imaging, the user selects a transmit power or the system uses a pre-set contrast agent imaging transmit power. Unlike tissue imaging or imaging of contrast agents at high MI, low MI imaging of contrast agents can be more challenging. Returned signals can be weak, and a user may often search for a preferred transmit power level. The user subjectively determines a transmit power level that minimizes bubble destruction but maintains a sufficient signal-to-noise ratio. This takes time and training. Systems that fix, or preset, the transmitted power levels for an examination can improve the efficiency of an examination. However, the preset values may not be optimal. Preset values may be sub-optimal due to different patient types, different clinical applications, or different contrast agents.

BRIEF SUMMARY

The present invention is defined by the following claims, and nothing in this section should be taken as a limitation on those claims. By way of introduction, the preferred embodiments described below include methods and systems for setting a contrast agent imaging transmit power. Automated determination and setting of the transmit power for low MI imaging provides efficient examination. The automated setting may be improved. Different transmit powers are tested to determine the highest or a higher power that minimizes contrast agent destruction or maximizes contrast agent specificity. By using different transmit powers for different spatial locations, such as interleaving the transmit powers on a line-by-line basis, samples for setting the transmit power may be obtained more quickly and accurately than sequential acquisition for the same spatial locations.

In a first aspect, a method is proved for setting a transmit power level to image contrast agents. First and second data are acquired from first and second scan lines, respectively, in a scan region. The first and second data are responsive to first and second transmit powers, respectively. The first transmit power is different than the second transmit power, and the first scan line different than the second scan line. The first data is compared with the second data. A third transmit power is set in response to the comparison for contrast agent imaging.

In a second aspect, a method is provided for setting a transmit power level to image contrast agents. Different transmit powers are interleaved as a function of scan line within a scanned region. Destruction of contrast agents is detected in response to one of the different transmit powers. A contrast agent imaging transmit power level is automatically set equal to or less than the one of the different transmit powers associated with destruction of contrast agents.

In a third aspect, an ultrasound system is provided for setting a transmit power level to image contrast agents. A transmit amplifier connects with a transducer. A processor is operable to set a contrast agent imaging transmit power of the transmit amplifier. The contrast agent imaging transmit power set as a function of a comparison of first and second data acquired in response to scan line interleaving of first and second transmit powers, respectively.

In a fourth aspect, a method is provided for setting a transmit power level to image contrast agents. A first relationship of contrast agent signal to tissue signal associated with a first transmit power is determined. A second relationship of contrast agent signal to tissue signal associated with a second transmit power is determined. The second transmit power is different than the first transmit power. The first and second relationships are compared. A contrast agent imaging transmit power is set in response to the comparison.

In a fifth aspect, a method is provided for setting a transmit power level to image contrast agents. First and second data are detected as a function of contrast agent specificity in response to first and second transmit powers, respectively. A maximum specificity of the first and second data is identified. A contrast agent imaging transmit power level is automatically set as a function of a one of the first or second transmit powers associated with the maximum specificity.

In a sixth aspect, an ultrasound system is provided for setting a transmit power level to image contrast agents. A transmit amplifier connects with a transducer. A processor is operable to set a contrast agent imaging transmit power of the transmit amplifier. The contrast agent imaging transmit power set as a function of a comparison of first and second relationships of contrast agent signal with tissue signal in response to first and second transmit powers, respectively.

Further aspects and advantages of the invention are discussed below in conjunction with the preferred embodiments.

BRIEF DESCRIPTION OF SEVERAL VIEWS OF THE DRAWINGS

In the figures, like reference numerals designate corresponding parts throughout the different views.

DETAILED DESCRIPTION OF THE PREFERRED EMBODIMENTS

Automated determination and setting of an ultrasound system transmit power is provided for low MI contrast agent imaging. A region is scanned with different transmit powers interleaved as a function of scan line. By comparing data associated with the different transmit power levels, a contrast agent imaging transmit power generally minimizing destruction of contrast agents and maximizing signal-to-noise ratio is automatically determined. Alternatively or additionally, contrast agent specificity is detected at different power levels. Rather than relying on detection of contrast agent destruction, the ratio of contrast agent to tissue signal is detected. For harmonic imaging, the transmit power associated with the maximum ratio provides desired imaging and may avoid destruction of contrast agents.

Figure 1:
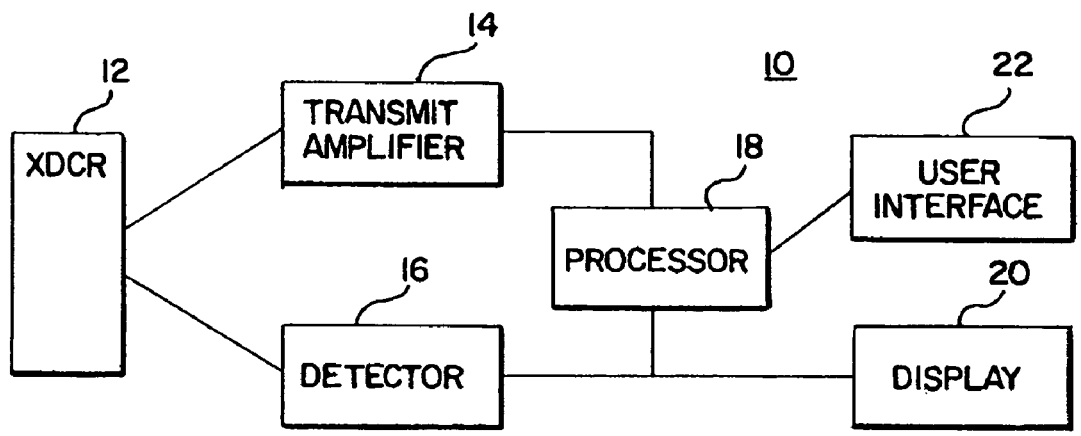
FIG. 1 is a block diagram of one embodiment of a system for setting a transmit power level.

FIG. 1 shows an ultrasound system 10 for setting a transmit power level to image contrast agents. The system 10 includes a transducer 12, a transmit amplifier 14, a detector 16, a processor 18, a display 20 and a user interface 22. Additional, different or fewer components may be provided, such as a multiple detectors associated with B-mode and flow imaging. In one embodiment, the system 10 is a medical diagnostic ultrasound system, such as the 128X®D, Aspen, ™ Sequoia® or Sonoline® ultrasound systems from Siemens Medical Systems, Inc. or another ultrasound system.

The transducer 12 is a single element or multiple elements of piezoelectric material. In alternative embodiments, the transducer 12 comprises capacitive membrane structures. For multiple elements, the transducer 12 is a linear, curved linear or multidimensional array. Other transducers for converting between electrical and acoustic energy can be used. The transducer 12 outputs acoustic waveforms at powers set by the transmit amplifier 14.

The transmit amplifier 14 connects with the transducer 12 and is a variable amplifier, digital to analog converter or other analog or digital device for changing or increasing a power, peak voltage or other power characteristic of a transmit waveform. In alternative embodiments, the transmit amplifier 14 comprises a voltage divider or other device for reducing the power associated with the transmit waveform. A separate transmit amplifier 14 is provided for each system channel or transducer element, but one transmit amplifier 14 can be used for a plurality of channels or elements. In one embodiment, the transmit amplifier 14 applies apodization for transmitting along a beam and is included as part of a transmit beamformer, such as disclosed in U.S. Pat. No. 5,675,554, the disclosure of which is incorporated herein by reference.

The transmit waveforms output from the transmit amplifier 14 are converted to acoustic energy by the transducer 12. Echo signals responsive to the acoustic energy and any contrast agents are received by the transducer 12. The transducer 12 converts the echo signals into electrical signals or data. As used herein, data includes one or more digital samples or analog information. After receive beamformation or other receiving technique, data is provided to the detector 16.

The detector 16 is a loss of correlation detector, B-mode detector, Doppler detector, flow detector or other detector for detecting a characteristic to be used to set the transmit power. The detector 16 may be a same detector used for imaging contrast agents. Alternatively, the detector 16 is used for setting the transmit power and is separate from detectors for imaging. The detector 16 detects contrast agent destruction, such as through loss of correlation, and/or contrast agent specificity. When contrast agents are destroyed or disrupted during two or more different transmit events, the received data have a loss-of-correlation (LOC). The second data is different than the first data. In one embodiment, three separate transmissions and receptions for each spatial location have same or similar characteristics, but different waveforms may be transmitted. The received data are weighted, such as with a [1-2 1] filter. Three pulses provide the minimal number of transmit events without introducing significant tissue flash. Fewer or a greater number of pulses can be used for each detected datum.

Other loss of correlation detection sequences are possible. For example, many sequences used for traditional color flow imaging provide loss of correlation detection. Sequences that detect motion with imaging modes such as color Doppler velocity (CDV) or color Doppler energy (CDE) also detect loss of correlation. Detectable energy or velocity originates from differences between two or more pulses. Other methods using two or more receive pulses after two or more pulses are transmitted can be used.

Other detection techniques may be used. For example, B-mode, intensity, amplitude or power detection is used. As another example, harmonic techniques or nonlinear imaging techniques are implemented by the detector 16. Phase or pulse inversion techniques, such as transmitting two waveforms of opposite polarity in sequence and then summing or subtracting the received signals with or without weighting, may be used. Other techniques for identifying information at a harmonic, including subharmonics (e.g. ½ f), fractional harmonics (³⁄₂ f) and/or integer harmonics (e.g. 2 f), of a fundamental transmit frequency band (f) may be used.

Detection techniques may be based upon detecting an increase in signal strength or a decrease in signal strength. When contrast agents are destroyed by one pulse, a second pulse may not echo from any contrast agent. The returned signal is less for the second pulse. Conversely, when some contrast agents are disrupted, an encapsulating shell cracks and releases an inner gas. This inner gas can be more reflective than the shell, returning a signal that is stronger.

For detecting specificity, the detector 16 detects contrast agent signal and tissue signal. Contrast agent signal is primarily responsive to contrast agents, but may include information from other sources. Similarly, tissue signal is primarily responsive to tissue, but may include information from other sources. Contrast agent signal may be identified using loss-of-correlation, harmonic imaging or other techniques. For example, a pulse or phase inversion second harmonic imaging technique is used to obtain contrast agent signal. One of the component pulses or received signals is used without combination to obtain tissue signal. Alternatively, a separate pulse is used for tissue signal.

The processor 18 is one or more of an application specific integrated circuit, a general processor, a digital signal processor, a control processor or other device operable to set a contrast agent imaging transmit power of the transmit amplifier 14. In response to user input initiating automatic transmit power setting or to software, the processor 18 determines the contrast agent imaging transmit power as a function of a comparison of information, such as sequentially acquired data, data acquired along different scan lines in an interleaved transmission and/or data indicating a relationship of tissue and contrast agent signals. For example, the processor 18 compares first and second detected data, such as loss of correlation detected data, associated with different transmit powers and different scan lines to determine a transmit power associated with destruction or non-destruction of contrast agent. As another example, the processor 18 compares or generates and compares tissue and contrast agent signals to determine a transmit power associated with a more optimum contrast agent specificity. The comparison and setting of the contrast agent imaging transmit power is performed automatically by the processor 18. User input to initiate or override the automatic setting may be provided.

In one embodiment, the processor 18 is operable to set the contrast agent imaging transmit power of the transmit amplifier as a function of a comparison of data acquired in response to scan line interleaving of different transmit powers. For example, the contrast agent imaging transmit power is set less than a greater of the second and first transmit powers where the greater transmit power is the lowest transmit power associated with detected destruction of contrast agents.

In another embodiment, the processor 18 is operable to set a contrast agent imaging transmit power of the transmit amplifier as a function of a comparison of different relationships of contrast agent signals with tissue signals in response to different transmit powers. For example, the processor 18 determines first and second specificities for first and second data associated with first and second different transmit powers. The contrast agent imaging transmit power is set to a transmit power associated with a highest ratio of the contrast agent signal to the tissue signal (i.e., a greater one of the first and second specificities).

Once the contrast agent imaging transmit power is set, data representing contrast agents is displayed on the display 20 for diagnostic medical imaging. Real-time or quickly repetitive transmissions and imaging is provided by avoiding significant destruction of contrast agent. More contrast agent specific information is displayed by increasing the contrast agent specificity. The transmit power may be periodically adjusted to continue avoiding destruction or increasing specificity or may be adjusted to cause destruction or decrease specificity.

Figure 2:
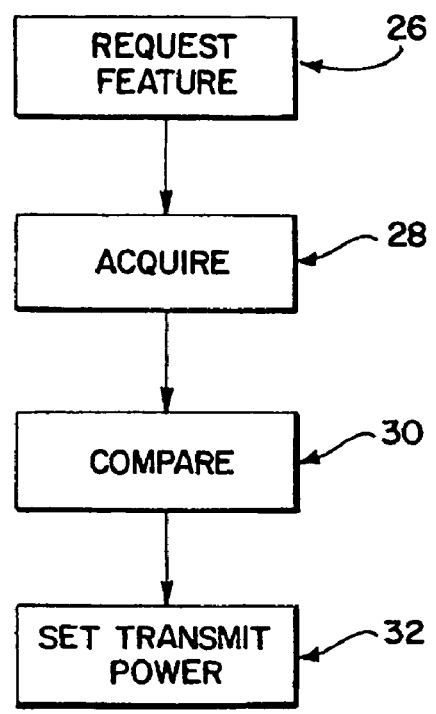
FIG. 2 is a flow chart diagram of one embodiment of a method for setting a transmit power level.

FIG. 2 illustrates a method for setting a transmit power level to image contrast agents. An optimal transmitted power level for a contrast agent examination is automatically determined after the contrast agent has entered the ultrasonic scan plane. Signal characteristics detected after contrast agent disruption or destruction or contrast agent specificities are used to determine the transmit power level.

In act 26, the transmit power setting feature of the system 10 (FIG. 1) is requested. For example, a user depresses a button, depresses a foot pedal, selects a menu item or speaks (e.g. control through voice activation). The user may select between different automatic power algorithms, such as associated with contrast agent destruction, contrast agent specificity or both. As another example, the user selects contrast agent imaging software or software specific to a contrast agent imaging application. For harmonic imaging or other modes of imaging, the contrast agent specificity may be used with or without contrast agent destruction considerations. Alternatively, contrast agent destruction without consideration of contrast agent specificity is used. As yet another example, the request is generated by continuously active software. Contrast agents are injected into a patient before or after the request. In response to the request, any current imaging is interrupted or interleaved with the acquisition of data in act 28.

In act 28, first and second data are acquired sequentially. For example, two samples representing a same location at different times are acquired. As another example, transmissions and receptions to satisfy the detection technique (e.g. multiple pulses for each loss of correlation datum or multiple pulses for each harmonic datum) are performed over a set of lines within an image region or section of an image to acquire sets of data. Fewer lines demands less processing time, so in one embodiment the line density is a factor of one to four less dense than is used for B-mode tissue imaging. Other line or sample densities can be used and sufficient computing speed may not demand any reduction in line or sample density.

In one embodiment, the different data responsive to the different transmit powers are acquired from different locations for determining the contrast agent imaging power level. Different transmit powers are interleaved as a function of scan line within a scanned region. Different transmit powers are transmitted for different lines for a same frame of data at a substantially same time. Substantially same time includes transmission at different times for a same scan or frame of data. Each scan of a region or frame of data corresponds to image information for a particular time. Data from different scan lines in a scan region is acquired. The data is responsive to different transmit powers.

Figure 9:
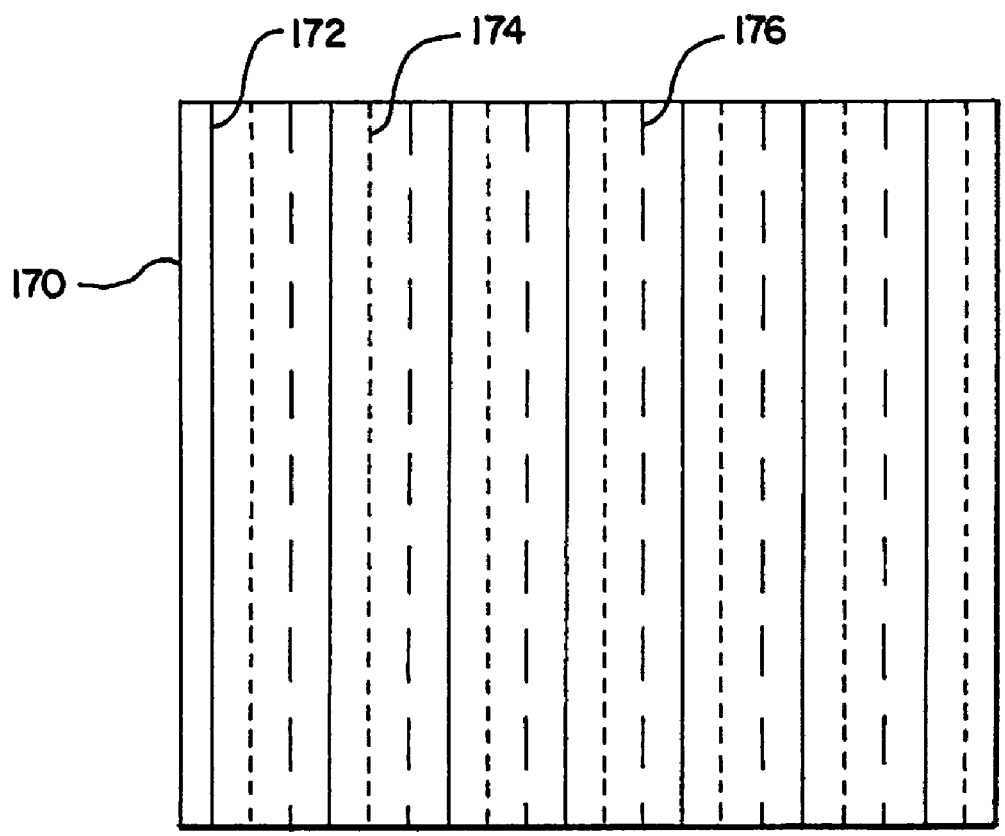
FIG. 9 is a graphical representation of one embodiment of a transmit pattern for interleaved transmit powers.

FIG. 9 shows a scan region 170 that is the same or different than the scan region used for contrast agent imaging. A plurality of scan lines 172, 174 and 176 are shown by dotted, dashed and solid lines. The scan lines 172, 174 and 176 are at a same or different density as used for contrast agent imaging. For example, the scan lines have about half the density as used for contrast agent imaging. The scan lines 172, 174 and 176 are spaced sufficiently apart to minimize or avoid overlapping point spread functions. The different scan lines 172, 174 and 176 correspond to transmissions of different power levels. A frame of data for the scan region 170 is acquired with at least two different transmit powers interleaved as a function of scan line position. FIG. 9 shows three different transmit powers interleaved along every third scan line 172, 174 and 176, but other numbers of transmit powers and/or relative frequencies of scan lines corresponding to the different powers may be used. The difference between transmit powers is spaced equally or unequally throughout range of possible or likely transmit powers. By using a greater number of transmit powers within a scan, the resolution of the power level setting may be increased. By using different transmit powers for different scan lines for a single scan of a region, information for determining the desired transmit power may be gathered more rapidly than transmitting with different powers to the same location. Transmissions for setting the transmit power may be less likely to effect subsequent contrast agent imaging or transmit power determinations.

In alternative embodiments, the different scan lines are associated with different scans of the region 170 or sequential frames of data. For example, two or more frames are sequentially acquired. Different scan lines or spatial locations are scanned for each of the sequential frames of data, such as where Frame 1 corresponds to scans along lines 0, 6, 12 . . . with power A; Frame 2 corresponds to scans along lines 2, 8, 14 . . . with power B, and Frame 3 corresponds to scans along lines 4, 10, 16 . . . with power C. For any given frame in the example above, the other scan lines are not scanned, but may be. One or more scan lines may be scanned more than once within a sequence of frames. More than one power level may be used within a given frame. By using sequential frames but scanning different spatial locations, the data for setting the transmit power is rapidly acquired while minimizing destruction of contrast agents. Rather than using different transmit powers as a function of scan line, data associated with different powers for different locations may be obtained as a function of depth spacing or depth and lateral spacing within a same or different scans of a region.

The data responsive to the different transmit powers is detected. For example, destruction of contrast agents is detected in response to one of the different transmit powers using a loss of correlation, harmonic imaging and/or contrast agent specificity. Contrast agent specificity indicates a relationship of contrast agent response to tissue response. For example, a ratio of contrast agent signals to tissue signals is determined. In one embodiment, the ratio is determined from harmonic imaging information at a harmonic frequency of a fundamental transmit band. An acoustic signal is transmitted at a fundamental frequency band. For harmonic imaging using multiple pulses, a plurality of pulses is transmitted in the same or different fundamental frequency band. For example, two pulses with opposite polarity are transmitted. Information is received in response to the transmissions at a harmonic of the fundamental frequency band. The information is received by filtering or combinations of signals from different transmit pulses. For example, received information from different pulses with different polarities is summed. The resulting sum is a contrast agent signal. Information from one of the pulses without combination is the tissue signal. The contrast agent signal and tissue signal are formed after detection or prior to detection.

The ratio of the contrast agent and tissue signals provides the contrast agent specificity. In the log domain, the ratio is obtained by subtracting the tissue signal from the contrast agent signal. Other relationships than a ratio may be used to indicate contrast agent specificity.

Data associated with different transmit powers, such as three or more transmit powers, and the same or different locations is acquired. The contrast agent specificity may be greater or lesser for different transmit powers. Relationships, such as the ratio, are determined for each of the different transmit powers.

In act 30, the first data is compared with the second data. Using one of various functions, the comparison indicates whether contrast agents have been destroyed or not been destroyed. For example, the first and second data are associated with different increasing transmit powers so that the first data is associated with non-destruction and the second data is associated with destruction or so that the first data is associated with destruction and the second data is associated with a lack of contrast agent. As another example, a decrease in values from the first to second data indicates destruction of contrast agent. Further examples are provided below in the discussion of FIGS. 3, 5 and 6.

In one embodiment, the comparison is performed by region. The scan region is divided into sub-regions, such as 3×3, 5×5 or other numbers of symmetrical or asymmetrical regions of the same or different sizes. The data division is used for each of the different data sets. An amount or number of contrast agent destruction events for each sub-region and each transmit power is determined. The resulting pattern for each transmit power is compared with the pattern for another transmit power. The optimum power is associated with the most desired pattern of bubble destruction or contrast agent specificity. For example, the pattern associated with some near field destruction of contrast agents but no or minimal middle field or far field destruction may be more desired than a pattern associated with no near field destruction. Other desired patterns based on the focal position or lateral field imaging conditions may be desired.

In the embodiment using contrast agent specificity, the different relationships of tissue to contrast agent response are compared. A maximum contrast agent specificity is identified, such as identifying the transmit power associated with the greatest ratio of contrast agent signal to tissue signal. For harmonic imaging of contrast agents, the identified transmit power is likely below, but may be above, the acoustic power associated with destruction of contrast agents. The most optimal transmit power may be identified by comparing both contrast agent destruction and contrast agent specificity.

Once destruction of contrast agent or non-destruction of contrast agent is determined, the transmit power for contrast agent medical diagnostic imaging is set in act 32. In response to the comparison, the contrast agent imaging transmit power is set as a function of a transmit power associated with one of the sets of data or an experimentally determined and stored transmit power is used. In one embodiment, the mechanical index or power level is indicated to the user on the display 20 (FIG. 1).

In the embodiment using contrast agent specificity, the contrast agent imaging transmit power level is automatically set as a function of the transmit power associated with the maximum detected specificity. For example, the same transmit power level is used in response to the comparison. The transmit level for imaging is different than transmit powers associated with a lesser desired specificity. The maximum detected specificity is associated with a specific location, multiple locations (e.g., an average), a specific region, or the entire scanned region.

Figure 3:
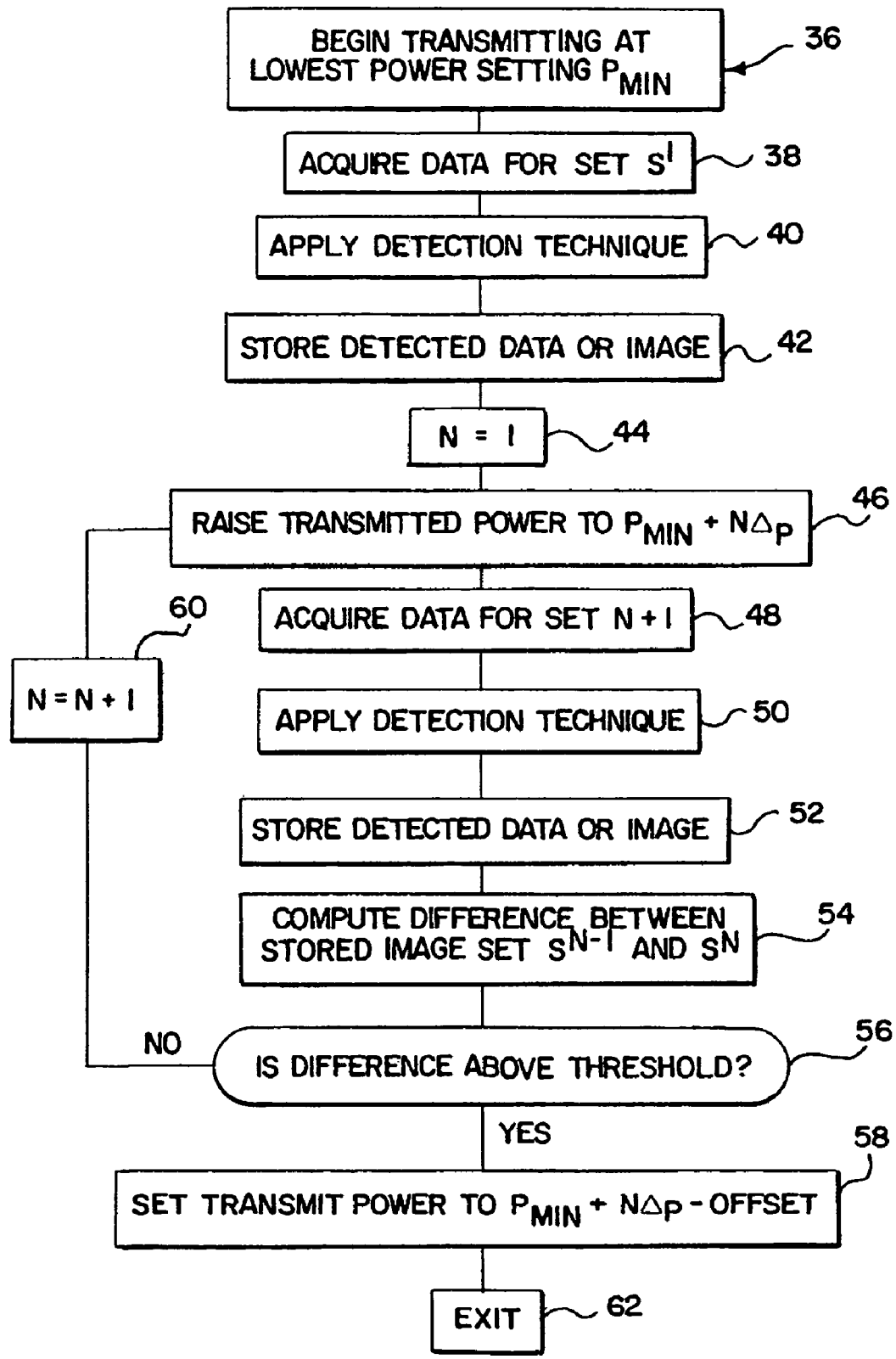
FIG. 3 is a flow chart diagram of a further embodiment of the method of FIG. 2.

FIG. 3 is a flow chart of one embodiment for setting a transmit power to image contrast agents. The transmit power is repetitively increased from a low power until destruction of contrast agents or desired specificity is detected. Acquisition of data is separated by a fixed delay or spatial locations. The contrast imaging transmit power level is then set to be less than the lowest transmit power associated with the destruction of contrast agents.

In act 36, an initial transmit power P is set to the minimum possible, $P_{min}$, power. The minimum is determined as a percentage of the maximum allowed power or a decibel value relative to the maximum allowed power. Alternatively, a preset low but non-minimum transmit power is initially used.

Data, such as data set $S^1$ is acquired in act 38 and detected in act 40. The detected data or pre-detected data is stored in act 42. A transmit power variable N is set to one in act 44, representing the initial acquisition of data associated with a first transmit power.

In act 46, the transmit power level is increased by an increment $\Delta p$. The increment is small, such as associated with 1/20 of the maximum transmit power or associated with an amplification resolution of the transmit amplifier 14 (FIG. 1). Other increments can be used, including increments that vary as a function of N or other variable.

Figure 4:
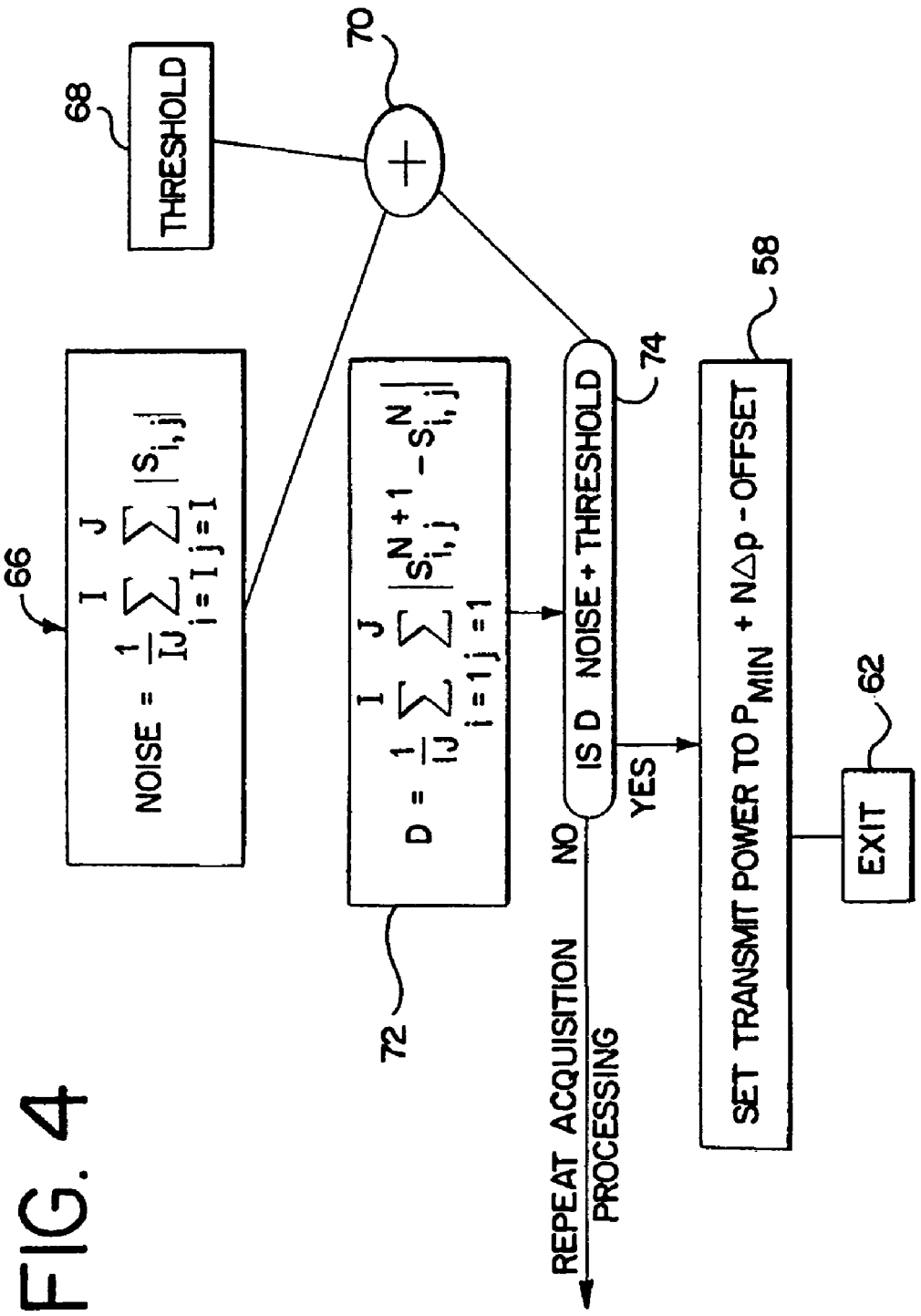
FIG. 4 is a flow chart diagram of one embodiment of a computation of the method of FIG. 3.

In act 48, another or second set of data is acquired using the higher transmit power. The acquired data is detected in act 50 and stored in act 52. After two sets of data are acquired, the sets of data are compared in act 54. In one example comparison, a difference between the sets of data is computed. Different methods for determining the difference may be dependent on the hardware or software used. FIG. 4 shows one embodiment for calculating the difference. An average difference between data representing the same or similar spatial locations is calculated, but other difference functions may be used as shown in act 72 where for each set S, the subscripts i and j define the location within a 2D plane with each superscript denoting the numbered set. The average may be extended into three dimensions.

As shown in FIGS. 3 and 4, the difference information is compared to a threshold in act 56, 74. In the embodiment of FIG. 3, the threshold is a predetermined threshold based on experimental expectations of a particular contrast agent, imaging application, imaging settings, transducer, patient characteristic, other variable or combination thereof. In the embodiment of FIG. 4, the threshold is determined dynamically. A noise level is measured as a function of spatial locations in act 66. For example, the system transmitters are turned off and the received signals are measured as noise. An average noise is calculated. The noise value is added to a threshold 68 in act 70. The difference data is compared to the noise and threshold value in act 74. Other dynamic threshold calculations may be used, such as thresholds based on transmit power or other variables.

As shown in FIGS. 3 and 4, if the comparison indicates no or minimal destruction of contrast agent, data acquisition is repeated. In particular, if the average difference is less than the threshold value in act 56, 74, then the value of N in incremented by one in act 60. The transmit power is increased again in act 46, another set of data responsive to the increased transmit power is acquired, detected and stored in acts 48, 50 and 52. The two most recently acquired sets of data are compared by computing a difference in act 54. If the difference is not significant as indicated by the threshold in act 56, the transmit power is increased again and the acts of acquiring and processing data are repeated yet again. Alternatively, a plurality of different powers, such as three or more are used to acquire a frame of data along different scan lines. By using power settings over a broad range of possibilities, repetition on a frame by frame basis may be limited, minimize or avoided.

Once the transmit power is increased so that contrast agents are destroyed or sufficient specificity occurs, the comparison of the sequentially acquired sets of data or data for different locations (e.g., scan lines associated with different transmit power) indicates a difference greater than the threshold in act 56. The contrast agent imaging transmit power is then set in act 58. The contrast agent imaging transmit power is set less than the greater of the two most recently used transmit powers. The contrast agent imaging transmit power is less than the transmit power associated with destruction of contrast agent. In one embodiment, the transmit power for contrast agent imaging is set to the first identified transmit power for contrast agent destruction, plus the cumulative sum of the incremental increases, and minus an offset (e.g. $P_{min}+N\Delta p-offset$). The offset value is selected to avoid destruction of contrast agent. A static offset value, such as equal to $\Delta p$ or a predefined value determined from experimentation or other means, is used. Alternatively, the offset value varies as a function of one or more variables. In yet another alternative, the transmit power is set to be at or near the transmit power associated with the greatest specificity. In act 62, the system 10 (FIG. 1) exits the algorithm to set the transmit power and begins or continues imaging contrast agents for medical diagnosis.

As an alternative to acts 54 and 56, each set $S^N$ is compared against a threshold to determine if destruction or sufficient specificity has occurred. If the value of the set $S^N$ is above the threshold, the transmit power is set, otherwise a new set $S^{N+1}$ is acquired with act 60. As another alternative, multiple sets S may be acquired in act 60 before any comparisons (act 56) are made, such as by using scan line power level interleaving. With this approach, the computations (act 54) and comparisons (act 56) may be delayed until the desired sets are acquired. As an example, the sets for each desired transmit power, $P_{min}, P_{min}+\Delta p, \ldots P_{min}+N\Delta p, P_{max}$ are acquired, and then processing steps for making a decision may be executed. These steps include one or more of detection (act 50), storage (act 52), difference calculations or other calculations (act 54), and a decision based on threshold(s) (act 56).

Figure 5:
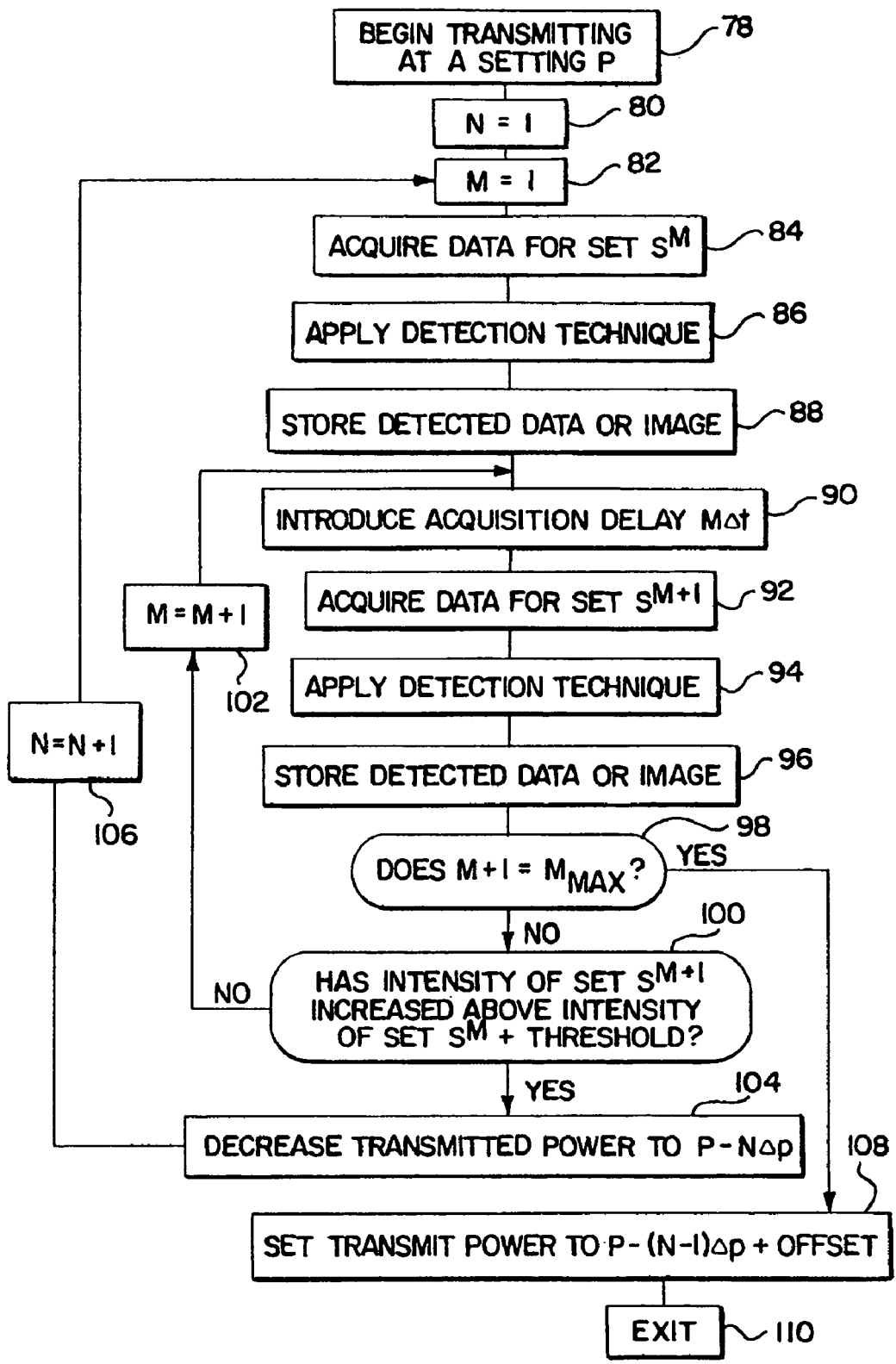
FIG. 5 is a flow chart diagram of another further embodiment of the method of FIG. 2.

FIG. 5 shows another algorithm for setting the transmit power level to image contrast agents. A high transmit power is used initially. Sets of data are acquired with an increasing delay between each set of data. Once return of contrast agent to the region due to the delay is detected, the transmit power is decreased. Once a transmit power is low enough to avoid destroying contrast agents, the delay reaches a maximum without detecting a change between sets of data. The contrast agent imaging transmit power is set as a function of the transmit power associated with no or minimal destruction of contrast agents.

In act 78, the transmit power is set to a maximum or other higher transmit power likely to destroy contrast agents. A power level variable N is set to one in act 80, and a time variable M is set to one in act 82. A first set of data is acquired, detected and stored in acts 84, 86 and 88.

In act 90, no or little acoustic energy is transmitted during a delay period $M\Delta t$, such as one second, one cardiac cycle (e.g. a cycle indicated by an ECG or Doppler data) or other interval. After the delay period, another set of data is acquired, detected and stored in acts 92, 94 and 96. In act 98, the time variable or the delay is checked against a maximum value. If the time variable or delay is not at a maximum, then the two data sets are compared in act 100. The intensities, average value or other characteristic of the data sets are compared. If the characteristic of the last acquired set of data is the same or lower than the previously acquired data set characteristic, then the acquisition is repeated. In particular, the time variable or delay is incremented. After the incremented delay of act 90, another data set is acquired, detected and stored in acts 92, 94 and 96. The check of act 98 and comparison of act 100 are repeated.

The acquisition of two sets of data responsive to different delays repeats until contrast agent is detected again. The variable temporal delay is used to determine when contrast agent is being significantly destroyed. During continuous imaging where contrast agent is actively entering the scan plane of interest, the amount of time between interrogations at high power levels dramatically changes the amount of returned ultrasonic echoes. If the transmitted power levels are high enough to destroy a significant quantity of the available contrast agent in the scan plane and the time between excitation events is small, an insignificant amount of fresh contrast agent enters the scan plane. If the time between excitation events is increased, more contrast agents enter the scan plane and the returned signal levels increase. For a fixed transmit power level, a series of returned signals are acquired with increasing amounts of delay, or dead time, between acquisitions such that an insignificant change in the signals over all acquisitions indicates an insignificant amount of contrast agent destruction.

Once a significant amount of contrast agent destruction is identified in act 100 (i.e. the characteristic of the last acquired data set is greater than the characteristic of the previous data set plus a threshold), the transmit power is decreased in act 104. For example, the transmit power level, P, is decreased by $N\Delta p$, where $\Delta p$ is an increment amount based on hardware limitations or experiments. After N is incremented in act 106, acts 82-104 are repeated. If the comparison of act 100 indicates return or destruction of additional contrast agent, the transmit power is decreased and a series of new acquisitions with variable delays between acquisitions are repeated.

The variable delay and decreasing transmit power nested processes are repeated until return or destruction of contrast agent is not detected after the increasing delays. If the comparison of the data sets indicates a similar or smaller intensity or other characteristic after the maximum delay, then the current transmit power level is not significantly destructive. No or few contrast agents are destroyed. In act 98, the delay or time variable is detected as the maximum.

The contrast agent imaging transmit power is set once the intensities of the sets of data are independent of the delays.

The contrast agent imaging transmit power is set to the current transmit power (i.e. the first transmit power associated with no destruction of contrast agent) or as a function of the current transmit power in act 108. For example, an offset is added to the transmit power where the offset is less than the increments in transmit power or where the offset is a negative offset. In act 110, the system 10 (FIG. 1) exits the algorithm to set the transmit power and begins or continues imaging contrast agents for medical diagnosis.

Other algorithms for setting the transmit power for contrast agent imaging based on decreasing transmit powers may be used. For example, in a simple binary search, a maximum power level is set initially. If the maximum level is destructive, the transmit power is reduced by half. Depending on whether contrast agent destruction is detected, the transmit power is set to either ¼ or ¾ of the maximum power. The process repeats for finer and finer transmit power adjustments until a desired transmit power is identified, such as a maximum non-destructive or a minimum destructive transmit power. Two, three or more iterations may be used. This process speeds up the convergence of the algorithm, decreasing the response time. As another example, the process shown in FIG. 3 decreases the transmitted power as the algorithm proceeds, but either a decrease or an increase in transmit power may be used.

Figure 6:
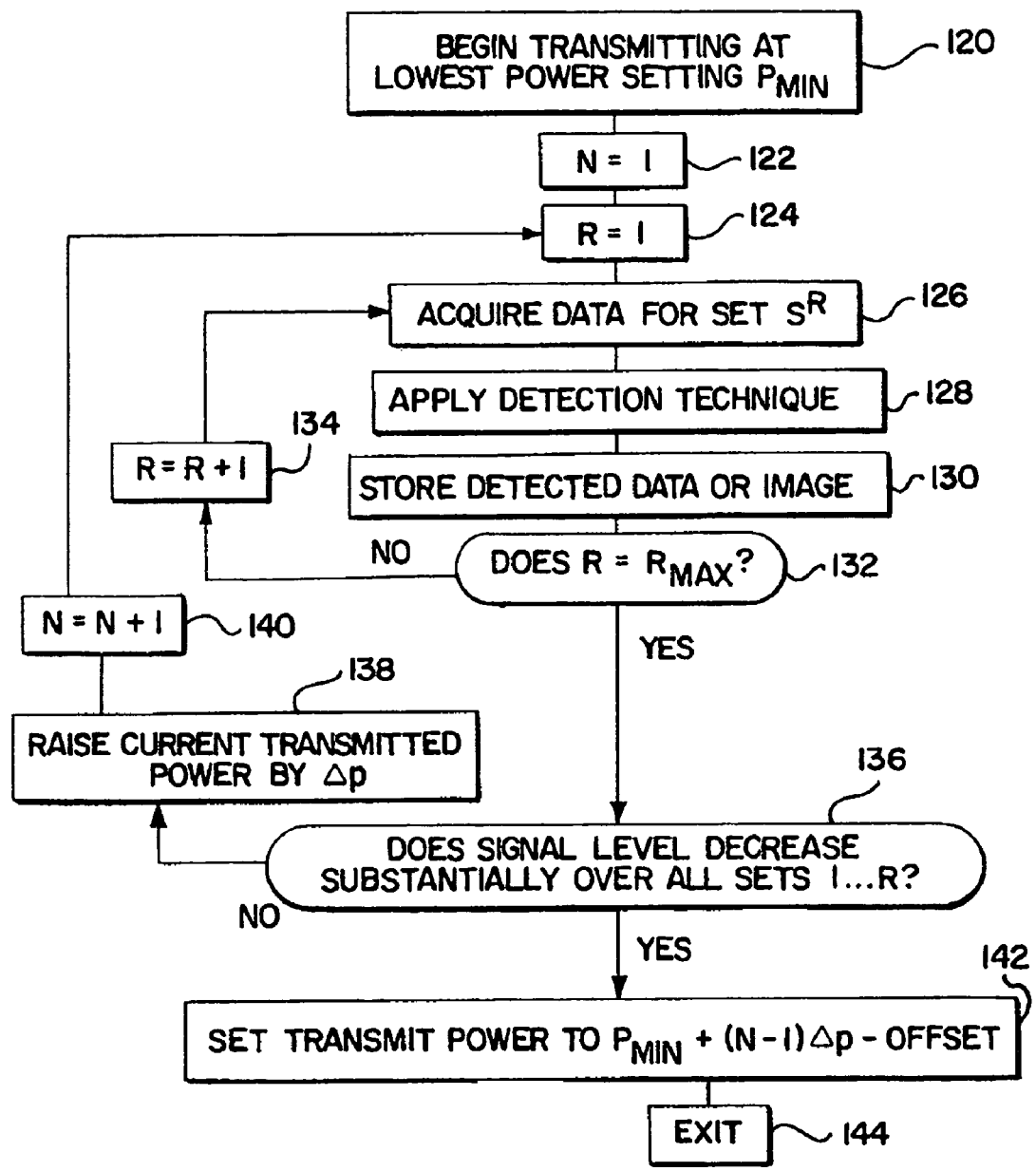
FIG. 6 is a flow chart diagram of yet another further embodiment of the method of FIG. 2.

FIG. 6 shows another process for setting a transmit power level to image contrast agents. Starting from a low transmit power, a series of data sets are acquired between each increment in transmit power. By comparing the data sets, a change in contrast agent destruction is monitored. At the first transmit power that destroys contrast agents, the change between data sets is greater. The contrast agent imaging transmit power is set as a function of the transmit power when the change indicates contrast agent destruction.

In act 120, the transmit power is set to a low or a lowest power. A power level variable, N, is set to one in act 122, and a repetition variable, R, is set to one in act 124. A set of data is acquired, detected and stored in acts 126, 128 and 130. In act 132, the repetition variable is compared to a maximum value. If the maximum number of repetitions has not been performed, then the repetition variable is incremented in act 134 and another set of data is acquired, detected and stored in acts 126, 128 and 130. The process repeats until the maximum number of repetitions, such as 2 or more, are performed. Multiple sets of data are acquired in response to a same transmit power.

In act 136, the sets of data are compared. For example, the signal level, intensity, average signal level or other characteristics of the data sets are compared. In one embodiment, a change in the average signal level over a plurality or all of the sets of data is determined. A linear or non-linear change is approximated, such as determining a slope associated with a linear change.

If the signal level or other characteristic does not change in a particular way, the transmit power and transmit power variable are incremented in acts 138 and 140. For example, if the average signal level does not decrease as a function of time, the transmit power is increased. Acts 124, 126, 128, 130, 132, 134 and 136 are repeated for each increase in transmit power.

When the comparison of act 136 indicates a substantial decrease or change, the contrast agent imaging transmit power is set. A substantial decrease in signal level indicates destruction of contrast agent. The contrast agent imaging transmit power is set in act 142 to the highest transmit power associated with no or minimal destruction of contrast agent plus an offset. Alternatively, no offset is provided or an offset is subtracted from the lowest transmit power associated with destruction of contrast agents or other transmit power. In act 144, the system 10 (FIG. 1) exits the algorithm to set the transmit power and begins or continues imaging contrast agents for medical diagnosis.

Various modifications to the algorithms of FIGS. 2-6 are possible, including additional, different, combined or fewer acts. For example, a single datum is acquired rather than a set of data. As another example, detection and/or storage of data are avoided or altered. As yet another example, either of increasing or decreasing transmit power levels are used to identify a highest transmit power level associated with minimal destruction of contrast agent. Non-destructive transmit powers other than the highest may be used as the contrast agent imaging transmit power. As yet another example, an amount of destruction or change in signal level is used to estimate the amount of any given increment or decrement in transmit power or to estimate the contrast agent imaging transmit power without further repetition. In another example, the contrast agent imaging transmit power is set to a lowest possible or other level associated with destroying contrast agent.

Figure 7:
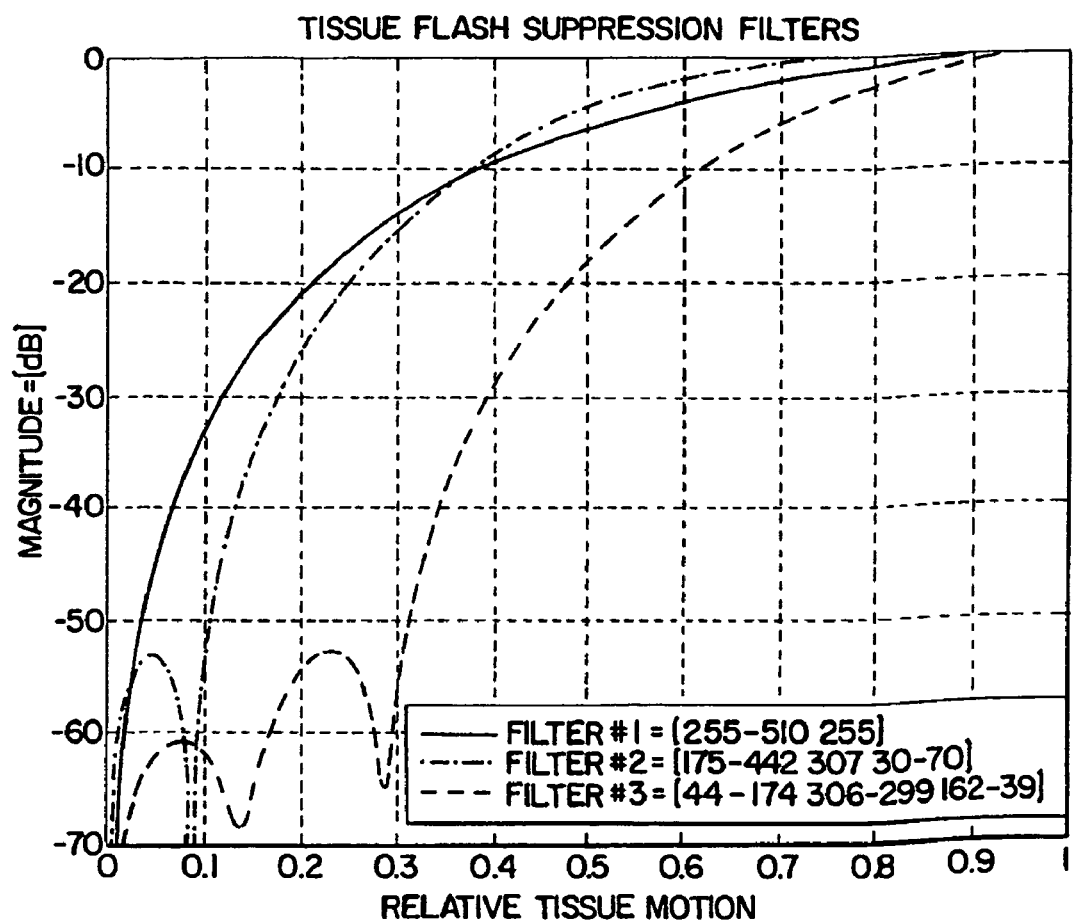
FIG. 7 is a graphical representation of various filter responses.

Tissue flash or artifacts from moving tissue may prevent or disrupt one or more of the algorithms discussed above, causing incorrect identification of the contrast agent imaging transmit power. The detection technique used may reduce tissue flash or motion artifacts. Using multiple pulse sequences increases the amount of tissue signal rejection for stationary and moving tissue signals. Clutter or wall filters, such as used for color Doppler imaging, also reduce these artifacts. Clutter filters with increased stopband attenuation and increased stopband bandwidth, centered around the signal returns for stationary tissue, improve the rejection of tissue flash. FIG. 7 shows the amount of returned signal strength versus tissue motion for three clutter filters where the maximum tissue motion is proportional to the interval between each of the multiple pulses used to detect returned signals. Increased time between pulses decreases the maximum detectable tissue motion and decreases the amount of tissue suppression for a given clutter filter. Larger, more positive magnitudes indicate less rejection. The filter coefficients for each of these particular finite impulse response (FIR) filters are shown in the legend. Filter 1 corresponds to the loss of correlation sequence of [1-2 1] described above. Filters 2 and 3 provide progressively more suppression of tissue signals, respectively. Other clutter filters may be used.

Signals generated from motion of contrast agent in addition to the desired signals from disrupted contrast agent may cause a lack of feature robustness or an incorrect transmit power setting. Detection techniques that utilize multiple pulses are sensitive to changes between pulses, such as contrast agent that is moving. Two possible solutions are: 1.) utilize different clutter filters and/or 2.) suppress signals from areas in the scanned region associated with simple motion. First, receive or clutter filters with increased suppression of signals generated by motion remove these undesirable signals. The same filters and examples discussed above for rejecting tissue motion may also be used to reject motion of contrast agent filled blood.

Figure 8:
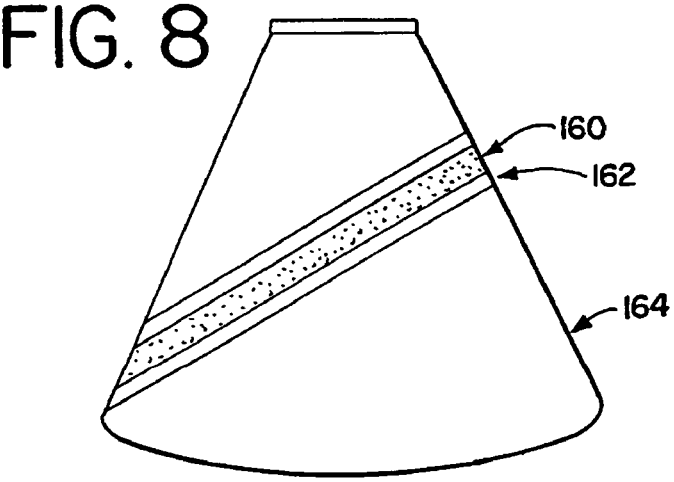
FIG. 8 is a graphical representation of one embodiment of a mask.

Second, areas associated with motion are masked (i.e. data associated with a masked area is deleted or not used). As an example, FIG. 8 shows an image of a vessel 160 in a scan plane 164. A low transmit power to avoid contrast agent disruption is used to acquire data. Blood moving within the vessel is detected, such as by loss of correlation or Doppler detection. A mask identifying regions or points associated with a threshold amount of movement is generated, such as the mask 162 over the vessel 160. The mask 162 may be expanded to include a buffer area around each point associated with movement, such as a buffer selected to account for possible motion of the transducer and/or vessel 160. Data from the masked areas or points is suppressed from the transmit power determinations discussed herein.

Areas of the imaged region with poor signal quality can reduce the robustness of the algorithms. A tissue detector or detector of acceptable signal quality may be used to identify areas with acceptable signal quality for use by the algorithms.

The automatically set contrast agent imaging transmit power may be optimal for one part of the image, or scan plane, but not optimal for another part. One solution is to alter one or more parameters, such as an offset, number of repetitions, delay increments, and/or transmit power increments. One of different stored combinations of parameters is selected by a user or selected as a function of the desired application, type of contrast agent, region of interest or other factor. Another solution is to identify areas or regions of interest in an image or scan plane. Areas associated with contrast agent in tissue (i.e., liver parenchyma), or large vessels or large cavities (i.e., aorta, ventricles, or atria) are identified by user input or processing received data. An example of a tissue detector is disclosed in U.S. Pat. No. 6,398,733 (Application Ser. No. 09/556,354) for "Medical Ultrasonic Imaging System with Adaptive Multi-Dimensional Back-End Mapping," the disclosure of which is incorporated herein by reference. The algorithm for setting the transmit power is altered as a function of the detected area, such as acquiring the sets of data for determining the transmit power from the detected area. Additionally or alternatively, parameters from a B-mode image are used to condition the automatic algorithm. For example, differences in B-mode intensity values discriminate one area in an image from another, to be included or excluded, from consideration.

Imaging of the heart is an example of an application that can benefit from selective use of subsections of an image for automatically determining a preferred transmit power. Identification of large blood-filled cavities, such as ventricles or atria, may be excluded, or included, as input to the algorithm based on movement of blood in the cavities, strong signals from blood in the cavities, or other means, The "acceptable" areas can further be limited and selected based on detecting unique signals from the myocardium based on a SNR detector or tissue detector. The identity of which subsections of an image should be used to set the transmit power may be dependent on the clinical application, as in the example here for cardiac imaging.

While the invention has been described above by reference to various embodiments, it should be understood that many changes and modifications can be made without departing from the scope of the invention. For example, different algorithms for setting the transmit power are provided. Statements of absolute quantities or effects (e.g. destruction or non-destruction of contrast agent) are used in general herein and include some contrary effects (e.g. some contrast agent surviving or being destroyed).

It is therefore intended that the foregoing detailed description be understood as an illustration of the presently preferred embodiment of the invention, and not as a definition of the invention. It is only the following claims, including all equivalents, which are intended to define the scope of this invention.

What is claimed is:

1. A method for setting a transmit power level to image contrast agents, the method comprising:
    (a) acquiring first and second data from first and second scan lines, respectively, in a scan region from a scan for a same frame of data, the first and second data responsive to first and second transmit powers, respectively, the first transmit power different than the second transmit power and the first scan line different than the second scan line;
    (b) comparing, with a processor, the first data with the second data;
    (c) setting a third transmit power based on the comparison for contrast agent imaging; and
    imaging contrast agents with the third transmit power; and
    (d) detecting the first and second data as a function of contrast agent specificity;
    wherein (b) comprises identifying a maximum specificity of the first and second data; and
    wherein (c) comprises setting the third transmit power as a function of the one of the first or second transmit powers associated with the maximum specificity.

2. An ultrasound system for setting a transmit power level to image contrast agents, the system comprising:
    a transducer;
    a transmit amplifier connected with the transducer; and
    a processor operable to set an contrast agent imaging transmit power of the transmit amplifier, the contrast agent imaging transmit power set as a function of a comparison of first and second data acquired in response to scan line interleaving of first and second transmit powers, respectively, in a scan for a same frame of data such that different scan lines are only insonified with only one of the first and second transmit powers, and wherein the processor is operable to determine first and second specificities for the first and second data, respectively, the contrast agent imaging transmit power being set as a function of a greater one of the first and second specificities.

3. A method for setting a transmit power level to image contrast agents, the method comprising:
    (a) determining a first ratio of contrast agent signal to tissue signal associated with data responsive to a first transmit power in a patient;
    (b) determining a second ratio of contrast agent signal to tissue signal associated with data responsive to a second transmit power in the patient, the second transmit power different than the first transmit power;
    (c) identifying, with a processor, a maximum of the first and second ratios;
    (d) setting a contrast agent imaging transmit power as a function of one of the first or second transmit powers associated with the maximum; and
    imaging the contrast agents as a function of the contrast agent imaging transmit power.

4. An ultrasound system for setting a transmit power level to image contrast agents, the system comprising:
    a transducer;
    a transmit amplifier connected with the transducer; and
    a processor operable to set an contrast agent imaging transmit power of the transmit amplifier, the contrast agent imaging transmit power set as a function of a comparison of first and second relationships of contrast agent signal with tissue signal in response to first and second transmit powers, respectively, and wherein the processor is operable to determine first and second specificities for the first and second data, respectively, the contrast agent imaging transmit power being set as a function of a greater one of the first and second specificities.

* * * * *